United States Patent [19]

Seebach et al.

[11] Patent Number: 4,745,218

[45] Date of Patent: May 17, 1988

[54] PROCESS FOR THE ENANTIOSELECTIVE PRODUCTION OF α-VINYL-α-AMINOCARBOXYLIC ACIDS

[75] Inventors: Dieter Seebach, Zürich; Theodor Weber, Vouvry, both of Switzerland

[73] Assignee: Degussa AG, Frankfurt am Main, Fed. Rep. of Germany

[21] Appl. No.: 917,071

[22] Filed: Oct. 8, 1986

[30] Foreign Application Priority Data

Oct. 10, 1985 [DE] Fed. Rep. of Germany ....... 3536146

[51] Int. Cl.$^4$ ............................................. C07C 101/04
[52] U.S. Cl. ..................................... 562/574; 548/301; 562/443; 562/445; 562/449
[58] Field of Search ................ 562/574, 445, 449, 443

[56] References Cited

U.S. PATENT DOCUMENTS 3,960,927  6/1976  Metcalf ................................. 562/574
4,585,892  4/1986  Seebach ............................... 562/574

*Primary Examiner*—Michael L. Shippen
*Attorney, Agent, or Firm*—Cushman, Darby & Cushman

[57] ABSTRACT

α-Vinyl-α-aminocarboxylic acids of the general formula:

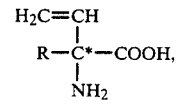

where * indicates a center of asymmetry and R is hydrogen, deuterium, lower alkyl, allyl, benzyl, or benzyl substituted 1 to 3 times by alkyl, alkoxy, fluorine or chlorine and produced enantioselectively from L-methionine by a multistep process.

2 Claims, No Drawings

PROCESS FOR THE ENANTIOSELECTIVE PRODUCTION OF α-VINYL-α-AMINOCARBOXYLIC ACIDS

SUMMARY OF THE INVENTION

The invention is directed to a process for the enantioselective production of α-vinyl-α-amino-carboxylic acids of the general formula:

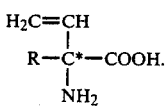

in which * is a center of asymmetry and R is hydrogen, deuterium, a methyl, ethyl, n-propyl, isopropyl, n-butyl, isobutyl, sec. butyl, allyl or benzyl group or a benzyl group substituted 1 to 3 times on the ring in any position by an alkyl, e.g., methyl, ethyl, or alkoxy, e.g., methoxy, ethoxy, group or by fluorine or chlorine which is characterized by acid hydrolyzing an imidazolidin-4-one of the general formula:

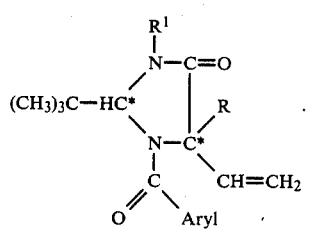

in which * and R are as defined above, R¹ is a methyl or ethyl group and aryl is a phenyl or substituted phenyl group, e.g., tolyl.

To carry out the process of the invention, first L-methionine is converted in known manner, e.g., in the process described in German OS 3334855 and related Seebach U.S. Pat. No. 4,585,892 (the entire disclosure of which is hereby incorporated by reference and relied upon) into an imidazolidin-4-one of the general formula:

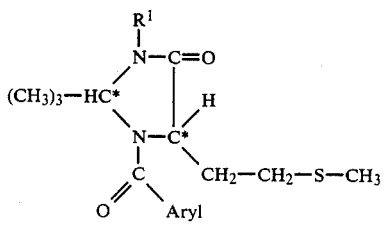

wherein *, R¹, and aryl have the above stated meanings and this compound reacted with an oxidizing agent. In this way, the thioether group is converted into a sulfoxide or sulfone group. As oxidizing agent, there can be employed hydrogen peroxide in a solvent such as formic acid or acetic acid ("in situ percarboxylic acids") or preformed percarboxylic acids, such as performic, peracetic, perpropionic acid, the latter, e.g., as a solution in benzene, or m-chloroperbenzoic acid. Periodates also can serve as the oxidizing agent. The oxidation reaction is suitably carried out at a temperature between 0° and 50° C., preferably between 20° and 30° C.

In the case of the oxidation with hydrogen peroxide, the procedure can be carried out in such manner that the imidazolidin-4-one of general formula (VI) is dissolved in formic acid or acetic acid, hydrogen peroxide in a 3 to 5 fold molar excess dosed in and for completion of the reaction the mixture stirred further for about 3 to 5 hours. Then the acid is neutralized, for example, with soda solution, the oxidation product extracted with a solvent non-miscible with water, such as methylene chloride, and the solvent evaporated off.

If preformed carboxylic acids are employed as oxidation agent, the process suitably is to introduce the imidazolidin-4-one of general formula (VI) in portions into the particular percarboxylic acid. As diluent, there can be used, for example, formic acid, acetic acid, or benzene. Suitable solvents for m-chloroperbenzoic acid above all are chlorinated hydrocarbons. Subsequently, the acid is again neutralized or the m-chlorobenzoic acid which is insoluble in chlorinated hydrocarbons is filtered off, if necessary the oxidation product extracted and the solvent or extraction agent evaporated.

In the case of oxidation with a periodate, there is preferably used as solvent or diluent mixtures of water and lower alcohols, such as methanol, ethanol, or propanol. Suitably, the imidazolidin-4-one of general formula (VI) is dissolved in the alcohol and an aqueous solution of the periodate, preferably sodium periodate, added. After a post reaction time of about 3 to 5 hours, the solvent is distilled off, the residue taken up in a solvent non-miscible with water and the salt washed out with water. Then the organic phase is evaporated.

The residue of crude oxidation product remaining in each case after evaporation of the solvent or extraction agent is then, without further purification, taken up in a high boiling solvent and stirred at a temperature between 170° and 250° C., preferably between 190° and 220° C. Thereby, fragmentation occurs to the 5-vinyl-5H-imidazolidin4-ones of the general formula:

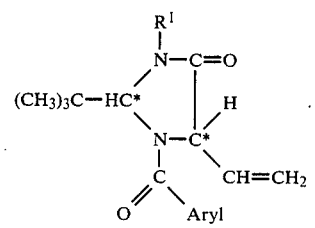

in which *, R¹, and aryl are as defined above. As high boiling solvent there can be used, for example, saturated aliphatic or alicyclic hydrocarbons, e.g., hexane, octane, decane, and cyclohexane, chlorobenzenes, e.g., monochlorobenzene or dichlorobenzene, xylenes, mesitylene or tetralin. The heating can be carried out, if necessary, under pressure. With sufficiently high boiling point of the solvent employed, however, operation can be at normal pressure.

After the end of the fragmentation, the solvent is evaporated off under reduced pressure and the residue remaining is purified by flash chromatography. Thus, there is obtained the analytically pure imidazolidin-4-one of general formula (III) in very good yields.

This can be converted into the imidazolidin-4-one of general formula (III) where R has the above-defined meanings except hydrogen or deuterium by alkylation with an alkylation of the general formula:

R²—X   (IV).

wherein R² has the meanings stated for R except hydrogen and deuterium and X indicates a group which is removed from the series, chloride, bromide, iodide, mesylate, trifluoromethylsulfonate, or tosylate.

For carrying out the alkylation, the imidazolidin-4-one of general formula (III) is reacted with a strong base of the general formula:

M—Y   (VII).

wherein M is lithium, sodium, or potassium and Y is hydrogen or a n-butyl, tert.butylate, amino, dimethylamino, diethylamino, di-n-propylamino, di-isopropylamino, di-(trimethylsilyl)-amino or phenyl group. This reaction is suitably carried out in such manner that there is added the strong base of general formula (VII) in an amount of 1.0 to 1.1 equivalent, all at once or within a few minutes to a solution of the imidazolidin-4-one in an inert solvent. Suitable inert solvents, for example, are ethers, such as diethyl ether, di-n-propyl ether, methyl tert.butyl ether or tetrahydrofuran, and also hydrocarbons such as n-pentane, n-hexane, or cyclohexane. Optionally, there can also be employed mixtures of such ethers and hydrocarbons.

As strong bases of general formula (VII), there can be employed, for example, butyl lithium, phenyl lithium, sodium hydride, potassium tert.butylate or N,N-disubstituted lithium amides. Preferably, there is used butyl lithium and lithium diisopropylamide. Optionally, the lithium diisopropylamide can be formed in situ from butyl lithium and N,N-diisopropylamine. The most suitable reaction temperatures are between −80° and 0° C.

In this reaction intermediate enolate is formed, which subsequently, directly, suitably likewise again at a temperature between −80° and 0° C. is further reacted with the alkylating agent of general formula (IV), which suitably is used in a 1.5 to 2.5 fold molar excess, based on the originally employed imidazolidin-4-one of general formula (III).

In this alkylation reaction, there is formed the imidazolidin-4-one of general formula (II), in which R is as defined above except for hydrogen and deuterium, in good chemical yields and practically homogeneous stereochemically.

Correspondingly, the imidazolidin-4-one of general formula (III) through reaction with a compound giving up deuterium ions (D⁺) can be converted into the imidazolidin-4-one of general formula (II) in which R is deuterium.

To carry out this reaction, the imidazolin-4-one of general formula (III) is first again converted with a strong base of general formula (VII) into an enolate. This enolate is then brought to reaction with a compound giving up deuterium ions. The latter must be sufficiently acid that the enolate thereof can split off a D⁺ion. As suitable compounds giving up deuterium ions there can be used, for example, D₂O, deuteriated methanol or ethanol, DCl or deuterotrifluoroacetic acid.

Alternatively, imidazolidin-4-ones of general formula (II), in which R is as defined above except hydrogen can be produced by first reacting an imidazolidin-4-one of general formula (VI), in the manner described above for the imidazolidin-4-one of general formula (III), with an alkylating agent of general formula (IV) or a compound giving up deuterium ions (D⁺) to form an imidazolidin-4-one of the general formula:

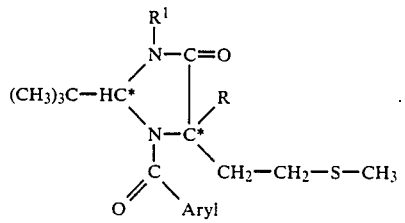

in which *, R¹, and aryl are as defined above and R is as defined above except for hydrogen, and then this compound, as described above for the imidazolidin-4-one of general formula (VI), is oxidized and subsequently fragmented.

The imidazolin-4-one of general formula (II) obtained according to one of the procedures described is finally hydrolyzed under acid conditions to the α-vinyl-α-aminocarboxylic acid of general formula (I). This occurs suitably through heating with a relatively concentrated mineral acid to a temperature between 150° and 200° C. under pressure. As acids above all there are employed 10 to 36 weight percent hydrochloric acid or 20 to 48 weight percent aqueous hydrobromic acid.

The hydrolysis mixture is cooled off, if necessary, filtered, extracted with methylene chloride, and the aqueous phase evaporated in a vacuum. The residue is taken up in water and in known manner dehydrohalogenated with the help of an ion exchanger (cation exchanger). The aqueous solution remaining of the α-vinyl-α-aminocarboxylic acid of general formula (I) is evaporated, and, if necessary, purified further chromatographically. There are thus obtained the optically pure, crystalline α-vinyl-α-aminocarboxylic acids.

The process of the invention accordingly opens up an outstanding access to optically pure α-vinyl-α-aminocarboxylic acids based on L-methionine. Such α-vinyl-α-aminocarboxylic acids are of continually increasing importance because of their properties as enzyme inhibitors and as antibiotics.

The process of the invention is explained in more detail through the following examples.

Unless otherwise indicated, all parts and percentages are by weight.

The process can comprise, consist essentially of the stated steps with the recited materials.

DETAILED DESCRIPTION

Example 1

(a) Production of (S)-N-(2′, 2′-Dimethyl-propylidene)-methionine Mono-Methylamide There were added to 40.0 grams (247 mmoles) of (S)-methionine mono-methylamide dissolved in 100 ml of n-pentane 27.5 ml (250 mmoles) of pivalaldehyde. The reaction mixture was boiled on the water separator until the formation of water ended (3 hours). The solvent was removed under reduced pressure and there remained behind 52.2 grams (92% of theory) of (S)-N-(2′, 2′- dimethylpropylidene)-methionine mono-methylamide which was further processed without further purification.

(b) Production of (2S,5S)-1-Benzoyl-2-tert.butyl-3-methyl-5-(3'-thiabutyl)imidazolidin-4-one A solution of 23.0 grams (100.0 mmoles) of the (S)-N-(2', 2'-dimethyl-propylidene)-methionine monomethylamide produced in (a) in 30 ml of methanol were treated with cooling to 0° C. with 60 ml of a saturated methanolic hydrochloric acid and stirred for 30 minutes at 0° C. and subsequently for 2 hours at 25° C. The solvent was removed at 25° C. under reduced pressure and the residue taken up in 100 ml of methylene chloride. The methylene chloride solution was treated at 0° C. with 11.6 ml (100 mmoles) of benzoyl chloride and 27.7 ml (200 mmoles) of triethylamine. After warming to 25° C., the reaction mixture was washed twice, each time with 150 ml of soda solution and once with 100 ml of water. The organic phase was dried over MgSO4, the methylene chloride distilled off in a vacuum and the residue dried for 1 hour at 50° C. and 0.065 mbar. Yield of (2S,5S)-1-benzoyl-2-tert.butyl-3-methyl-5-(3'-thiabutyl)-imidazolidin-4-one; 31.5 grams (94% of theory). For further purification, the product was recrystallized twice from diethyl ether. Melting Point: 129° C.

(c) Production of (2S,5S)-1-Benzoyl-2-tert.butyl-3-methyl-5-vinyl-imidazolidin-4-one To a solution of 5.02 grams (15 mmoles) of the (2S,5S)-1-benzoyl-2-tert.butyl-3-methyl-5-(3'- thiabutyl)-imidazolidin-4-one produced according to (b) in 30 ml of glacial acetic acid there were added at 25° C. 5.7 grams (60 mmoles) of a 35 weight percent aqueous solution of hydrogen peroxide and subsequently stirring was continued for 4 more hours at 25° C. The reaction mixture was extracted with a total of 300 ml of methylene chloride. The extract was washed twice, with 150 ml of saturated soda solution each time, and once with 150 ml of water. After drying, the organic phase over MgSO4 and evaporation of the solvent the solid residue without further purification was treated with about 60 ml of xylene and heated to 200°-210° C. for 2 hours in a sealed tube.

The xylene was distilled off under reduced pressure and the residue was purified by flash chromatography (ether/CH2Cl2 in the volume ratio 8:1). There were obtained 3.20 grams (78% of theory) of (2S,5S)-1-benzoyl-2-tert.butyl-3-methyl- 5-vinyl-imidazolidin-4-one which for further purification was recrystallized from a mixture of CH2Cl2/pentane in the volume ratio 1:1.

Melting Point: 169° to 171° C.
$[\alpha]_D^{25}$: +110.0° (c=1; CHCl3)
IR (KBr): 2990s, 1710s, 1650s, 1380s cm$^{-1}$
$^1$H-NMR (CDCl3): 7.65–7.30 (m, 5H aromatic);
5.69 (s, 1H, H-C(2));
5.30–4.55 (m, 4H, vinyl);
3.12 (s, 1H, H3C-N);
1.10 ppm (S, 9H, t-Butyl).

(d) Production of (2S,5R)-1-Benzoyl-2-tert.butyl-3,5-dimethyl-5-vinyl-imidazolidin-4-one There were slowly added 5.5 mmoles of lithium to a solution of 6.5 mmoles of diisopropylamine in 20 ml of tetrahydrofuran cooled to −78° C. After 30 minutes, the thus obtained solution of lithium diisopropylamide solution at −78° C. was dropped into a solution in 20 ml of tetrahydrofuran of 1.42 grams (5 mmoles) of the (2S,5S)-1-benzoyl-2-tert.butyl-3-methyl-5-vinyl-imidizolidin-4-one produced according to part (c) of this example. Thereby, the initially colorless solution became colored deep red. After stirring for 30 minutes at −78° C., there were added 0.78 ml (12.5 mmoles) of methyl iodide and stirring at 0° C. continued for an additional 5 hours. The lightly yellow reaction mixture was poured into 200 ml of saturated aqueous ammonium chloride solution. Then it was extracted with a total of 250 ml of methylene chloride and the organic phase was washed with 150 ml of sodium chloride solution.

After drying the organic phase over magnesium sulfate, the solvent was drawn off at 40 mbar on a rotary evaporator and the solid residue was recrystallized from CH2Cl2/pentane in the volume ratio 1:1. There were obtained 1.24 grams (83% of theory) of (2S,5R)-benzoyl-2-tert.butyl-3,5- dimethyl-5-vinyl-imidazolidin-4-one.

Melting Point: 117° to 117.5° C.
$[\alpha]_D^{25}$: −58.3° (c=1; CHCl3)
IR (KBr): 2980 m, 2880 m, 1700s, 1640s, 1605m, 1585m cm$^{-1}$
$^1$H-NMR (CDCl3): 7.58–7.30 (m, 5H aromatic); 6.21 (dd, J$_1$=11, J$_2$=18, 1H, CH-C(5)); 5.79 (s, 1H, H-C(2)); 5.20 (dd, J$_1$=11, J$_2$=18, 2H, H2C=C(5)); 3.08 (s, 3H, H3C-N); 1.16 (s, 3H, H3C-C(5)); 1.10 ppm (s, 9H, t.Butyl).

(e) Production of (R)-2-Vinyl-alanine

A mixture of 0.493 gram (1.64 mmoles) of the (2S,5R)-1-benzoyl-2-tert.butyl-3.5-dimethyl-5-vinyl-imidazolidin-4-one produced according to part (d) of this example and about 15 ml of 6N hydrochloric acid was heated for 4 hours in a bomb tube at 160° C. After extraction with 30 ml of CH2Cl2 the aqueous phase was evaporated on a rotary evaporator. The crude hydrochloride was taken up in a little water and dehydrohalogenated by means of a cation exchanger (Dowex 50W×8). The pure (R)-2- vinyl-alanine after a flash chromatography (CH3OH/CH2Cl2/NH3 in the volume ratio 5:5 : 0.5) and evaporation of the eluate was obtained as a white crystalline compound in a yield of 37% of theory.

Melting Point: 228°+229° C.
$[\alpha]_D^{25}$: −32.8 (c=0.733; H2O )
$^1$H-NMR (D2O ) (HDO=4.7 ppm): 6.20–5.80 (m, 1H,$\underline{CH}$=CH2); 5.60–5.20 (m, 2H, CH-CH2); 1.52 ppm (s, $\overline{3H}$, CH3).

EXAMPLE 2

(a) Production of (S)-N-(2', 2'-dimethyl-propylidene)-methionine Mono-Methylamide The procedure was the same as in Example 1(a).

(b) Production of (2S,5S)-1-Benzoyl-2-tert.butyl-3-methyl-5-(3'-thiabutyl)-imidazolidin-4-one The procedure was the same as in Example 1(b).

(c) Production of (2S,5R)-1-Benzoyl-2-tert.butyl-3,5-dimethyl-5-(3'-thiabutyl)imidazolidin-4-one 10.6 mmoles of a 1M solution of lithium diisopropylamide in tetrahydrofuran at −60° C. were added to 3.34 grams (10.0 mmoles) of the (2S,5S)-1- benzoyl-2-tert.butyl-3-methyl-5-(3'-thiabutyl)-imidazolidin-4-one produced according to Example 2(b) dissolved in 60 ml of tetrahydrofuran. Thereby, the solution became deep red in color. After a further 15 minutes stirring at −60° C., there were added 0.9 ml (15.0 mmoles) of methyl iodide. The now weakly yellow reaction mixture was allowed to warm to room temperature, poured into 100 ml of about half saturated aqueous NH₄Cl solution and extracted with a total of 200 ml of diethyl ether. The combined organic extracts were washed with water, dried over MgSO₄ and freed from solvent under reduced pressure. The residue was recrystallized from a mixture of diethyl ether and n-pentane in a volume ratio 1:1, whereupon there were obtained 2.36 grams (66% of theory) of (2S,5R)-1-benzoyl-2-tert.butyl-3,5-dimethyl-5-(3'-thiabutyl)-imidazolidin-4-one.

Melting Point: 105° C.

$[\alpha]_D^{20}$: −71.9° (c=1; CHCl₃)

(d) Production of (2S,5R)-1-Benzoyl-2-tert.butyl-3,5-dimethyl-5-vinyl-imidazolidin-4-one There were dosed into a solution of 1.045 grams (3 mmoles) of the (2S,5R)-1-benzoyl-2-tert.butyl-3,5-dimethyl-5-(3'-thiabutyl)-imidazolidin-4-one produced according to Example 2(c) in 10 ml of methanol 0.666 gram (3.32 mmole) of sodium periodate dissolved in 4.5 ml of water and the mixture subsequently stirred for 4 hours at 25° C. After distilling off the solvent on the rotary evaporator the residue was treated with 30 ml of CH₂Cl₂, stirred with 10 ml of water and the organic phase was evaporated again. The solid residue was taken up directly in 10 ml of xylene and heated for 2 hours in a bomb tube at 210° C. After evaporation of the solvent and flash chromatography (ether/petroleum ether in a volume ratio of 2:1), there were isolated 0.852 gram (95% of theory) of diastereomer pure (2S,5R)-1-benzoyl-2-tert.butyl-3,5-dimethyl-5-vinyl-imidazolidin-4-one.

| C₁₈H₂₄N₂O₂ (300.40) | | | |
|---|---|---|---|
| | % C | % H | % N |
| Calculated: | 71.96 | 8.05 | 9.32 |
| Found: | 71.73 | 7.94 | 9.13 |

(e) Production of R-2-Vinyl-alanine

The procedure was as in Example 1(e).

EXAMPLE 3

(a) Production of (S)-N-(2'- 2'-Dimethyl-propylidene)-methionine Monomethylamide The procedure was as in Example 1(a).

(b) Production of (2S,5S)-1-Benzoyl-2-tert.butyl-3-methyl-5-(3'-thiabutyl)-imidazolidin-4-one The procedure was as in Example 1(b).

(c) Production of (2S,5S)-1-Benzoyl-2-tert.butyl-3-methyl-5-vinyl-imidazolidin-4-one The procedure was as in Example 1(c).

(d) Production of (2S,5R)-1-Benzoyl-5-benzyl-2tert.butyl-3-methyl-5-vinyl-imidazolidin-4one In a manner analogous to Example 1(d), there were obtained from 1.43 grams (5 mmoles) of the (2S,5S)-1-benzoyl-2-tert.butyl-3-methyl-5-vinyl-imidazolidin-4-one produced according to Example 3(c) and 1.49 ml (12.5 mmoles) of benzyl bromide after 4 hours reaction time at −5° C. 1.18 grams (75% of theory) of (2S,5R)-1-benzoyl-5-benzyl-2-tert. butyl-3-methyl-5-vinyl-imidazolidin-4-one in a diastereomer purity of 87%.

Melting Point: 152° C.

$[\alpha]_D^{25}$: −27.5° (c=1; CHCl₃)

| C₂₄H₂₈N₂O₂ (376.50) | | | |
|---|---|---|---|
| | % C | % H | % N |
| Calculated: | 76.56 | 7.50 | 7.44 |
| Found: | 76.50 | 7.53 | 7.46 |

MS (EI): 361 (M⁺− 15, 0.3) 105 (100)

IR (KBr): 2870m, 1700s, 1630s, 1595w, 1570m cm⁻¹.

(e) Production of (R)-2-Vinyl-phenylalanine

From a mixture of 0.69 grams (1.8 mmoles) of the (2S,5R)-1-benzoyl-5-benzyl-2-tert.butyl-3-methyl-5-vinyl-imidazolidin-4-one produced according to Example 3(d) and 20 ml of 6N hydrochloric acid after 6 hours heating in a bomb tube at 180° C. after operating analogous to Example 1(e) and flash chromatography (CH₃OH/CH₂Cl₂/NH₃ in the volume ratio 6:4:0.5 there were obtained 20 mg (5% of theory) of (R)-2-vinyl-phenylalanine.

¹H-NMR (D₂O): 7.31 (m, 5H aromatic); 6.13 (dd, J₁=11, J₂=18. 1H, H-C(3)); 5.29 (m, 2H, H₂C(4)); 3.21 ppm (AB, J=15, 2H-Benzyl).

The entire disclosure of German priority application P.3536146.8 is hereby incorporated by reference.

What is claimed is:

1. A process for the enantioselective production of an α-vinyl-α-amino-carboxylic acid of the formula:

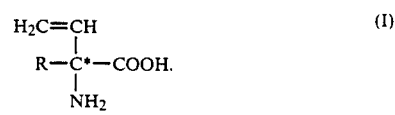

(I)

in which * is a center of asymmetry and R is hydrogen, deuterium, a methyl, ethyl, n-propyl, isopropyl, n-butyl, isobutyl, sec. butyl, allyl or benzyl group or a benzyl group substituted 1 to 3 times on the ring by an alkyl or alkoxy group or by fluorine or chlorine comprising producing an imidazolidin-4-one of the formula

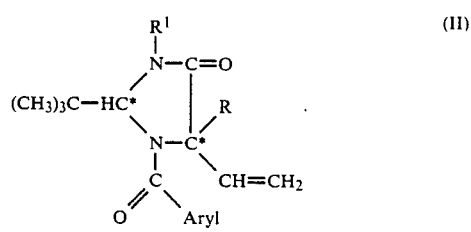

(II)

in which * and R are as defined above, R¹ is a methyl or ethyl group and aryl is a phenyl or substituted phenyl group by oxidation and subsequent fragmentation of an imidazolidin-4-one of the formula:

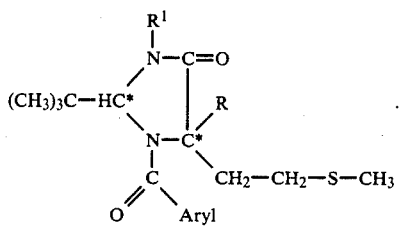

(V)

and then acid hydrolyzing the imidazolidin-4-one.

2. A process for the enantioselective production of an α-vinyl-α-amino-carboxylic acid of the formula:

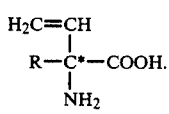

(I)

in which * is a center of asymmetry comprising producing an imidazolidin-4-one of the formula

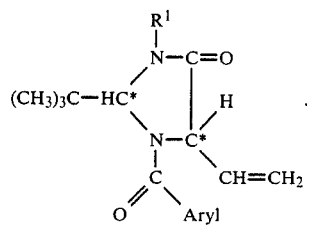

(III)

in which * is as defined above, $R^1$ is a methyl or ethyl group and aryl is a phenyl or substituted pheynyl group by oxidation and subsequent fragmentation of an imidazolidin-4-one of the formula:

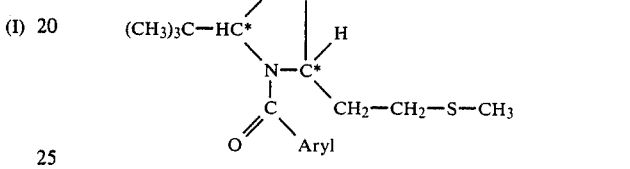

(VI)

and then acid hydrolyzing the imidazolidin-4-one.

* * * * *